United States Patent [19]

Klemann et al.

[11] Patent Number: 5,006,351

[45] Date of Patent: Apr. 9, 1991

[54] CYCLOHEXYL DIOL DIESTERS AS LOW CALORIE FAT MIMETICS

[75] Inventors: Lawrence P. Klemann, Somerville; John W. Finley, Whippany; Anthony Scimone, Cedar Grove, all of N.J.

[73] Assignee: Nabisco Brands, Inc., East Hanover, N.J.

[21] Appl. No.: 372,288

[22] Filed: Jun. 27, 1989

[51] Int. Cl.$^5$ .............................................. A23D 7/00
[52] U.S. Cl. .................................. 426/611; 426/601; 426/604; 426/804; 260/410; 560/231
[58] Field of Search ............... 426/601, 604, 611, 804; 260/410; 560/231

[56] References Cited

U.S. PATENT DOCUMENTS

| | | |
|---|---|---|
| 519,980 | 5/1894 | Winter . |
| 2,924,528 | 2/1960 | Barsky et al. .......................... 99/118 |
| 2,924,582 | 2/1960 | Mullins et al. ...................... 260/30.4 |
| 2,962,419 | 11/1960 | Minich ................................. 167/81 |
| 2,993,063 | 7/1961 | Alsop et al. ........................ 260/410.6 |
| 2,999,866 | 9/1961 | Starcher et al. ..................... 560/231 |
| 3,147,236 | 9/1964 | Port et al. ............................ 260/78.4 |
| 3,239,539 | 3/1966 | Bartlett et al. ........................ 560/194 |
| 3,495,010 | 2/1970 | Fossel .................................... 424/312 |
| 3,579,548 | 5/1971 | Whyte .................................. 260/410.7 |
| 3,600,186 | 8/1971 | Mattson et al. ............................ 99/1 |
| 3,637,774 | 1/1967 | Babayan et al. .................. 260/410.6 |
| 3,818,089 | 6/1974 | Bayley et al. ............................ 424/9 |
| 3,876,794 | 4/1975 | Rennhard ............................ 426/152 |
| 3,903,123 | 9/1975 | Henrick et al. ..................... 560/123 |
| 4,005,195 | 1/1977 | Jandacek ................................ 424/180 |
| 4,304,768 | 12/1981 | Staub et al. ........................... 424/180 |
| 4,508,746 | 4/1985 | Hamm .................................... 426/601 |
| 4,540,657 | 9/1985 | Krishnamurthy ................... 430/546 |
| 4,631,196 | 12/1986 | Zeller ................................... 426/580 |

FOREIGN PATENT DOCUMENTS

| | | |
|---|---|---|
| 1106681 | 8/1981 | Canada . |
| 205273 | 12/1986 | European Pat. Off. . |
| 233856 | 8/1987 | European Pat. Off. . |
| 254547 | 1/1988 | European Pat. Off. . |
| 923691 | 4/1963 | United Kingdom . |

OTHER PUBLICATIONS

Chemical Abstracts, 6403g, vol. 62, No. 6, 1965.
Okumura et al., "Synthesis of Various Kinds of Esters by Four Microbial Lipases" Biochimyca et Biophysical Acta, vol. 525, 1979, pp. 156–165.
Brockerhoff, H., et al., B. B. A. 212:92-101 (1970).
Iwai, M., and Tsujisaka, Y., in Borgstroem and Brockman's Lipases, Elsevier, New York, 1987, pp. 457–462.
Zaks, A., and Klibanov, A. M., 82 P.N.A.S. U.S.A. 3192–3196 (1985).
Bergelson, L. D., et al., 116 B.B.A. 511–520 (1965).
Booth, A. N., and Gros, A. T., 40 J.A.O.C.S. 551–553 (1963).
Dawson, G. W., et al., 22 Pestic. Sci. 17–30 (1988).
Goodman & Gilman's Pharmacological Basis of Therapeutics, 7th ed., Macmillan, 1002–1003 (1985).
Gurr, M. I., and James, A. T., Lipid Biochemistry, 3rd ed., Chapman Hall, 90–92 (1980).
Halliburton, W. D., et al. 13 J.B.C. 301–305 (1919).
Hamm, D. J., 49 J. Food Sci. 419–428 (1984).
Haumann, B. J., 63 J.A.O.C.S. 278–287 (1986).
LaBarge, R. G., 42 Food Tech. 84–90 (1988).
Lapworth, A., and Pearson, L. K., 13 J.B.C. 296–300 (1919).
Markley, K. S., ed., Fatty Acids, 2d ec., part 2, Kreiger 785–797 (1983).
Stryker, W. A., 31 Arch. Path. 670–692 (1941).

*Primary Examiner*—Donald E. Czaja
*Assistant Examiner*—Evan Federman

[57] ABSTRACT

Collectively called cyclohexyl diol diesters, the fatty acid diesters of cyclohexanediol, cyclohexenediol, and cyclohexdienediol and their dimethanol and diethanol counterparts, are edible, preferably partially digestible, fat replacements. Methods of using the new fat mimetics and food compositions incorporating them are described.

54 Claims, No Drawings

CYCLOHEXYL DIOL DIESTERS AS LOW CALORIE FAT MIMETICS

BACKGROUND OF THE INVENTION

This invention relates to the use of cyclohexyl diol diesters, notably the fatty acid diesters of cyclohexanediol, cyclohexane dimethanol and diethanol, cyclohexenediol, cyclohexene dimethanol and diethanol, and cyclohexdienediol and cyclohexdiene dimethanol and diethanol as edible, preferably partially digestible, fat replacements for foods and pharmaceuticals.

Since fats provide nine calories per gram compared to four calories per gram provided by protein or carbohydrates, major research efforts toward reduction of caloric intake for medical or health reasons have focused on ways to produce food substances that provide the same functional and organoleptic properties as fats, but not the calories.

A major strategy for developing low calorie replacement fats has been to structurally re-engineer natural triglycerides in such a way as to retain their conventional functional properties in foods, while removing their susceptibility toward hydrolysis or subsequent absorption during digestion. To this end, the the fatty acids attached to glycerol have been replaced with alternate acids (U.S. Pat. No. 3,579,548 to Whyte); groups have been inserted between the fatty acids and the glycerol backbone ("propoxylated glycerols", Eur. Pat. Ap. No. 254,547 to White and Pollard); the ester linkages have been replaced by ether linkages (U.S. Pat. No. 3,818,089 to Bayley and Carlson, and Can. Pat. No. 1,106,681 to Trost); the ester linkages have been reversed (U.S. Pat. No. 4,508,746 to Hamm); and the glycerol moeity has been replaced with an alternate alcohol (e.g., ethylene glycol in U.S. Pat. No. 2,924,528 to Barskey et al., and U.S. Pat. No. 2,993,063 to Alsop and Carr).

A second major approach to the development of a low calorie fat replacement has been to explore or synthesize nonabsorbable polymeric materials structurally unlike triglycerides, but having physical properties similar to edible fat. Mineral oil was disclosed as early as 1894 (U.S. Pat. No. 519,980 to Winter), and, more recently, polydextrose (U.S. Pat. No. 4,631,196 to Zeller), polyglucose and polymaltose (U.S. Pat. No. 3,876,794 to Rennhard), polysiloxane (Eur. Pat. Ap. No. 205,273 to Frye), jojoba wax (W. Ger. Pat. No. 3,529,564 to Anika), and polyethylene polymers (E. Ger. Pat. No. 207,070 to Mieth, et al.) have been suggested.

A third major strategy combines the first two. Rather than restructure triglyceride molecules or find a substitute structurally very dissimilar, this approach explores the use of various polyol esters, compounds which have numbers of fatty acid groups in excess of the three in conventional fat triglycerides, as nonabsorbable fat replacements. Fully esterified sugar alcohols were suggested as fat replacements during World War I (notably mannitol, Lapworth, A., and Pearson, L. K., and Halliburton, W. D., et al., 13 *J. Biol. Chem.* 296 and 301 (1919)); Minich suggested esterifying pentaerythritol a tetrahydric neopentyl sugar alcohol which can be formed from pentaerythrose, in 1960 (U.S. Pat. No. 2,962,419); and the Southern and Western Regional Research Laboratories of the U.S.D.A. investigated the feasibility of using amylose esters as new-type fats during the 1960's (see Booth, A. N., and Gros, A. T., 40 *J. Amer. Oil Chem. Soc.* 551 (1963) and the references cited therein). More recently, sucrose polyesters have been suggested (U.S. Pat. No. 3,600,186 to Mattson and Volpenhein). The caloric availability and digestibility of a series of dimeric and polymeric glycerides including diglyceride esters of succinic, fumaric, and adipic acids, and polymeric fats from stearic, oleic and short-chain dibasic acids were assessed by the U.S.D.A. group cited supra, and polyglycerol esters have since been suggested (U.S. Pat. No. 3,637,774 to Babayan and Lehman).

Nondigestible or nonabsorbable triglyceride analogues, polyol esters, and polymeric materials have proved disappointing as fat replacements when tested in feeding trials, where gastrointestinal side effects occurred, in some cases so extreme that frank anal leakage was observed (for recent reviews, see Hamm, D. J., 49 *J. Food Sci.* 419 (1984), Haumann, B. J., 63 *J. Amer. Oil Chem. Soc.* 278 (1986), and LaBarge, R. G., 42 *Food Tech.* 84 (1988)). Nondigestible fats act as a laxative and are expelled from the body, eliciting foreign body reactions like those early documented for mineral oil (Stryker, W. A., 31 *Arch. Path.* 670 (1941), more recently summarized in Goodman and Gilman's *Pharmacological Basis of Therapeutics*, 7th ed., Macmillan Pub. Co., N.Y. 1985, pages 1002-1003). Polyglycerol and polyglycerol esters, for example, suggested as fat replacements supra, have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, or incorporating saturated fatty groups, Eur. Pat. Ap. No. 233,856 to Bernhardt), and dietary fiber preparations have been incorporated into polysaccharide and/or polyolcontaining foodstuffs to help inhibit the diarrheal effect (U.S. Pat. No. 4,304,768 to Staub et al.).

SUMMARY OF THE INVENTION

An object of the present invention is to provide a fat mimetic having substantially fewer calories than normal fat. It is another object of the present invention to provide a fat replacement more compatible with normal digestion. It is a further object of the present invention to provide a fat replacement which can mimimize or avoid laxative side effects. In the preferred embodiment of this invention, it is a further object of the present invention to provide a partially digestible fat replacement which may, if desired, be engineered to provide food functional properties and desirable or essential fatty acids.

In the practice of this invention, cyclohexyl diol diesters, notably the fatty acid diesters of cyclohexanediol, cyclohexenediol, and cyclohexdienediol and their dimethanol and diethanol derivatives, comprise a new class of edible, preferably partially digestible, fat replacements for foods and pharmaceuticals.

DETAILED DESCRIPTION OF THE INVENTION

The fatty acid diesters of cyclohexanediol, cyclohexanedimethanol, cyclohexenediol, and cyclohexenedimethanol have been used outside the food industry as plasticizers and starting materials for polymers and resins (U.S. Pat. No. 2,924,582 to Mullins et al., U.S. Pat. No. 2,999,866 to Starcher and Tinsley, U.S. Pat. No. 3,147,236 to Port and Scholnick, U.S. Pat. No.

3,239,539 to Bartlett et al., and G.B. Pat. No. 923,691 to Jenkins et al.), as aphid pheromone derivatives (Dawson, G. W., et al. 22 *Pestic. Sci.* 17 (1988)), and as a photographic coupler solvent (U.S. Pat. No. 4,540,657 to Krishnamurthy). This invention is based upon the discovery that this group of diester compounds and their structural analogues are useful as low calorie fat mimetics in edible compositions.

Diol lipids, diacyl esters and mixed alkyl and alkenyl ester fatty acid derivatives of ethylene glycol, 1,2- and 1,3-propanediols, 1,3-, 1,4- and 2,3-butanediols, and 1,5-pentanediols, comprise a minor lipid component of some natural tissues, including mutton fat, fish liver, egg yolks, corn seeds, yeast, and rat liver (see Bergelson, L. D., et al., 116 *Biochim. Biophys. Acta* 511 (1966) and Gurr, M. I., and James, A. T., *Lipid Biochemistry*, 3rd ed., Chapman and Hall, New York, 1980). These natural diol lipids have linear backbones.

Diol lipids have not figured into reported edible fat replacement research which as focused, instead, on ways of providing fat replacements for triglycerides. In the practice of this invention, cyclohexyl diol diesters, compounds having cyclic backbones structurally distinct from diol lipids, but having two fatty acid substituents, comprise a new class of edible fat replacements.

The cyclohexyl diol diester compounds of the present invention can be defined by the following structural formula:

X—Q—X, where

Q is a cyclohexane, cyclohexene or cyclohexdiene ring backbone,

X is a —O—(CO)—R, —CH₂—O—(CO)—R, or —(CH₂)₂—O—(CO)—R side chain, and

R is, independently, an aliphatic group having 1 to 29 carbons.

The compounds of the present invention have six-carbon cyclic backbones which may be fully saturated or may have one or two double bonds. Two fatty acid residues are attached to the cyclic six-member backbones in ester linkage, or in ester linkage with one or two intervening methylene groups.

Thus, the compounds of this invention comprise fatty acid diesters of cyclohexanediol, cyclohexanedimethanol, and cyclohexanediethanol, which can be represented by the following structural formula,

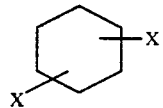

where

X is —O—(CO)—R, —CH₂—O—(CO)—R, or —(CH₂)₂—O—(CO)—R, and R is, independently, an aliphatic group having 1 to 29 carbons.

The compounds of the present invention further comprise fatty acid diesters of cyclohexenediol, cyclohexenedimethanol, and cyclohexenediethanol, which can be represented by the following structural formula,

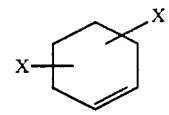

where

X is —O—(CO)—R, —CH₂—O—(CO)—R, or —(CH₂)₂—O—(CO)—R, and R is, independently, an aliphatic group having 1 to 29 carbons.

The compounds of the present invention also comprise fatty acid diesters of cyclohexdienediol, cyclohexdienedimethanol, and cyclohexdienediethanol, which can be represented by the following structural formula,

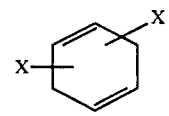

where

X is —O—(CO)—R, —CH₂—O—(CO)—R, or —(CH₂)₂—O—(CO)—R, and R is, independently, an aliphatic group having 1 to 29 carbons.

The compounds of this invention comprise cyclohexane, cyclohexene and cyclohexdiene diols and their dimethanol and diethanol counterparts, collectively referred to herein as "cyclohexyl diols," esterified with two fatty acids. The fatty acids may be attached in ester linkage, with or without one or two intervening methylene groups, anywhere on the cyclohexyl ring. The diester compounds of this invention may have ester groups attached to the same carbon atom, to vicinal carbons, or to distal carbons. Chemical formulae and descriptions include isomeric variations.

The term "fatty acids" used here means organic fatty acids containing a sufficient number of carbon atoms to provide for the physical properties commonly attributed to edible fats and oils. Fatty acids may be synthetic or natural, saturated or unsaturated, with straight or branched chains, and have from 2 to 30 carbon atoms. Denoted RCOOH, fatty acids thus provide the aliphatic R group in the formulae above. Examples of fatty acids are acetic, propionic, buryric, caproic, caprylic, pelargonic, capric, undecanoic, lauric, myristic, palmitic, stearic, arachidic, behenic, oleic, linoleic, linolenic, eleostearic, and arachidonic acids. Mixtures of fatty acids may also be used, such as those obtained from non-hydrogenated or hydrogenated sunflower, safflower, soybean, olive, sesame, peanut, palm kernel, cottonseed, palm, babassu nut, canola, rice bran, corn, butter, or other natural or processed oils. Specific fractions of natural or processed oils may also be used.

At least one R will have 7 to 29 carbon atoms (derived, as described above, from an acid having 8 to 30 carbons), and the remainder will be selected to provide a discernible fatty character in the compounds. Thus, most of the R groups have 3 or more carbon atoms (derived from acids having 4 or more carbons), with a percentage containing 3 to 22 (derived from acids having 4 to 23 carbons), more narrowly, 15 to 17 carbon atoms (derived from acids having 16 to 18 carbons). Where the R groups are fatty acid residues derived from natural oils, for example, safflower, sunflower, corn or soybean oil, 98% or more of the R groups are derived from fatty acids containing 16 to 18 carbon atoms, with 80% or more containing 18 carbon atoms.

The preferred cyclohexyl diol diesters of this invention are partially digestible, and typically provide from about 0.5 to 8.5, more narrowly 1.0 to 6.0 kcal/gram. In these preferred compounds, the side groups X show differential reactivity toward digestive enzymes, so that the compounds become more hydrophilic when catabolized. The cleaved residue R can be from an essential or nutritionally desirable fatty acid such as linoleic acid. The cleaved residue R can also be from a fatty acid with preventative or possibly curative effect for certain diseases or conditions, such as, for example, a conjugated linoleic acid isomer.

The compounds of this invention may be prepared using esterification techniques for diols such as those published and reviewed in Markley, K. S., *Fatty Acids*, 2nd. ed., part 2, Krieger Pub. Co., 1983, pages 785-797). These include reactions of the fatty acids, or the fatty acid derivatives, fatty acid chlorides or anhydrides, with the diols, and transesterification between fatty acid esters (e.g., fatty acid methyl esters) and the diols. A few specific syntheses have been reported; see, for example, 1,2-cyclohexanediol dilaurate (to be used as a polyvinyl chloride plasticizer) in Example 3, Belg. Pat. No. 616,274 (1962) and castor bean enzyme catalyzed oleic acid esterification of 1,2-, 1,3- and 1,4-cyclohexanediol in Velluz, L., and Saleau, P., 197 *Compt. Rendus.* 277 (1933).

A solvent may be employed in the syntheses. The term "solvent" means any material, including the reactants, that is liquid at the synthesis reaction temperature and pressure and will dissolve, suspend or hold the reactants in the reaction mixture in an amount effective to expedite contact for the desired esterification reaction to occur. Sample syntheses for some edible cyclohexyl diol diesters of this invention are included in the Examples section.

The synthesis reactions may be catalyzed. Example catalysts are alkali metal hydroxides such as potassium or sodium hydroxide or hydrides such as potassium or sodium hydride.

The cyclohexyl diol diesters of this invention may be incorporated either alone, or in combination with another fat and/or fat mimetic, into any food composition or used in conjunction with any edible material. The term "edible material" is broad and includes anything edible. Representative of edible materials which can contain the cyclohexyl diol diester compounds of this invention in full or partial replacement of natural fat are: frozen desserts, e.g., sherbet, ice cream, ices, or milk shakes; puddings and pie fillings; margarine substitutes or blends; flavored bread or biscuit spreads; mayonnaise; salad dressings; filled dairy products such as filled cream or filled milk; dairy or nondairy cheese spreads; coffee lighteners, liquid and dried; flavored dips; frying fats and oils; reformed and comminuted meats; meat substitutes or extenders; whipped toppings; compound coatings; frostings and fillings; cocoa butter replacements or blends; candy, especially fatty candies such as those containing peanut butter or chocolate; chewing gum; bakery products, e.g., cakes, breads, rolls, pastries, cookies, biscuits, and savory crackers; mixes or ingredient premixes for any of these; as well as flavor, nutrient, drug or functional additive delivery systems.

The following is a list of representative, but not limiting, examples of cyclohexyl diol diesters of this invention:

(1) Trans-1,2-Cyclohexane Dioleate

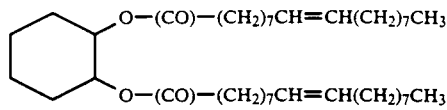

(2) Cis-1,2-Cyclohexane Dimyristate

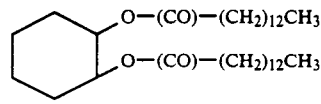

(3) Cis-1,2-Cyclohexanedimethane Dioleate

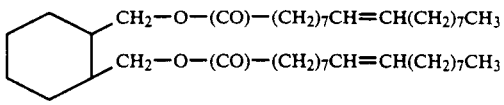

(4) Trans-1,2-Cyclohexanedimethane Di-10-Undecenate

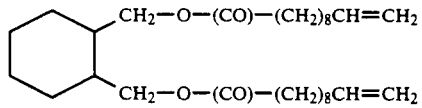

(5) 1,4-Cyclohexanedimethane Dioleate

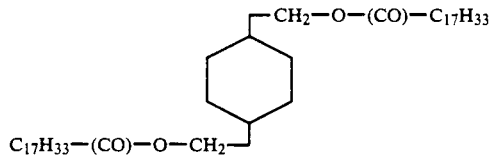

(6) 1,1-Cyclohex-3-enedimethane Di-10-undecenate

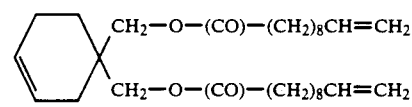

(7) 1,1-Cyclohex-3-ene Dioleate

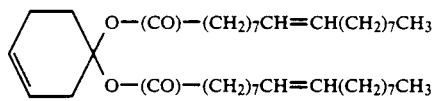

(8) 1,2-Cyclohex-4-ene Oleate Stearate

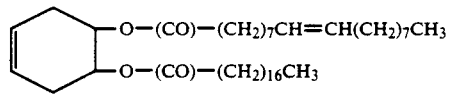

(9) 1,4-Cyclohex-2,5-diene Dimyristate

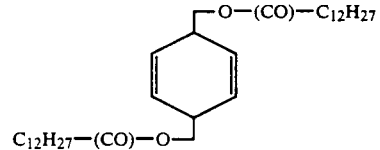

(10) 1,1-Cyclohex-3-ene Linoleate/Palmitate

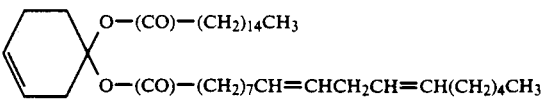

EXAMPLES

The following examples are presented to further illustrate and explain the present invention and should not be taken as limiting in any regard. Unless otherwise indicated, all parts and percentages are by weight (in both the synthesis and food recipe examples), and are based on the weight at the particular stage of the processing being described. The proton NMR spectra have assigned chemical shifts, multiplicities, and intensities consistent with the structures for which they are reported.

Example 1

Cis-1,2-Cyclohexanedimethane dioleate, a cyclohexyl diol diester of this invention, is synthesized in this example.

Oleoyl chloride (38 grams, 0.126 mole) is added dropwise, with stirring, to a solution of cis-1,2-cyclohexanedimethanol (9.7 grams, 0.067 mole) in 40 mL pyridine. After the addition is complete, 20 mL heptane is added to facilitate stirring. The mixture is filtered after one hour and the filtrate is washed with 5% HCl and water and then dried over anhydrous magnesium sulfate. Filtration and evaporation afford the title composition as an oil.

Proton NMR Spectrum in $CDCl_3$: (multiplicity, intensity, assignment): 5.35 (multiplet, 4 H, HC=CH), 4.07 (doublet, 4 H, O—$CH_2$), 2.30 (triplet, 4 H, O=C—$CH_2$), 2.02 (multiplet, 10 H, C=C—$CH_2$ and methine proton), 1.61, 1.52 and 1.31 (multiplets, 52 H, $CH_2$) and 0.89 (triplet, 6 H, $CH_3$).

Example 2

This example describes an alternate synthesis of cis-1,2-cyclohexanedimethane dioleate prepared in Example 1.

Oleoyl chloride (76 grams, 0.25 mole) and cis-1,2-cyclohexanedimethanol (19.4 grams, 0.134 mole) are combined in a flask containing a magnetic stir bar and fitted with a thermometer and a vacuum adapter. The solution is mixed under vacuum and warmed at 115° C. After 4 hours, the cyclohexyl diester product is filtered through a bed of Celite to obtain a light yellow oil.

Example 3

Trans-1,2-cyclohexane dioleate (also called trans-1,2-dioleoyloxycyclohexane), another cyclohexyl diol diester of this invention, is prepared in this example.

To a magnetically stirred solution of 10 grams (0.086 mole) trans-1,2-cyclohexanediol in 25 mL pyridine at 0° C. is added dropwise 45.5 grams (0.15 mole) technical grade oleoyl chloride. A precipitate of pyridinium chloride forms as the viscous mixture is stirred one hour. Upon cooling, the solid is removed by filtration and the dark solution is diluted with 100 mL ethyl acetate. This solution is washed four times with 50 mL 5% HCl each time, two times with 50 mL water, and dried over sodium sulfate. Filtration and evaporation of the solvent affords a residue which is subjected to flash chromatography over silica. Elution with 9:1 hexane ethyl acetate affords, after evaporation, the title composition (15.7 grams) as an oil.

Proton NMR Spectrum in $CDCl_3$: chemical shift in ppm (multiplicity, intensity, assignment): 5.35 (multiplet, 4 H, HC=CH), 4.81 (multiplet, 2 H, methine protons), 2.26 (triplet, H, O=C—$CH_2$), 2.02 (multiplet, 8 H, C=C—$CH_2$), 1.62, 1.59, 1.31 (multiplets, 52 H, —$CH_2$—) and 0.89 (triplet, 6 H, —$CH_3$).

Example 4

Cis and trans 1,4-cyclohexanedimethane dioleate (also called 1,4-bis(oleoyloxymethyl) cyclohexane), another cyclohexyl diol diester of this invention, is prepared in this example.

To a solution of 1.44 grams (0.01 mole) 1,4-cyclohexane dimethanol (Aldrich, mixture of cis and trans) in 10 mL pyridine is added 7 mL (ca. 0.021 mole) of oleoyl chloride (Fluka, technical grade). The reaction mixture is shaken overnight at ambient temperature, filtered, concentrated on a rotary evaporator and refiltered to afford an oil.

Proton NMR Spectrum in $CDCl_3$ chemical shift in ppm (multiplicity, intensity, assignment): 5.35 (multiplet, 4 H, HC=CH), 3.99–3.88 (two doublets: cis (J=5 Hz) and trans (J=7 Hz), 4 H, $CH_2$—$O_2C$), 2.29 (triplet, 4 H, $CH_2$—$CO_2$), 2.00 (multiplet, 8 H, $CH_2$—C=C), 1.60 (multiplet, 4 H, $CH_2$—C—$CO_2$), 1.30 (multiplet, 40 H, $CH_2$), 1.90–0.95 (multiplet, 10 H, ring protons), and 0.87 (triplet, 6 H, $CH_3$).

Example 5

1,1-Cyclohex-3-enedimethane di-10-undecenate (also called 1,1-bis(10-undecenoyloxymethyl)cyclohex-3-ene), another cyclohexyl diol diester of this invention, is prepared in this example.

To a solution of 2 grams (0.015 mole) 3-cyclohexene-1,1-dimethanol in 30 mL pyridine is added 7 mL 10-undecenoyl chloride. After shaking overnight at ambient temperature, the reaction mixture is filtered through silica, concentrated on a rotary evaporator, and refiltered through silica to afford an oil.

Proton NMR Spectra in $CDCl_3$: chemical shift in ppm (multiplicity, intensity, assignment): 5.79 (multiplet, 2 H, chain HC=CH), 5.67 and 5.57 (multiplets, 2 H, ring HC=C), 4.96 (multiplet, 4 H, C=$CH_2$), 3.96 (two AB spin systems, 4 H, $CH_2$—$O_2C$), 2.29 (triplet, 4 H, $O_2C$—$CH_2$), 1.90–2.02 (multiplets, 8 H, $CH_2$—C=C) and 1.30–1.60 (multiplet, 26 H, $CH_2$).

Example 6

Trans-1,2-cyclohexane dimyristate (also called trans-1,2-dimyristoyloxycyclohexane), another cyclohexyl diol diester of this invention, is prepared in this example.

To a magnetically stirred solution of 10 grams (0.086 mole) trans-1,2-cyclohexanediol in 25 mL pyridine at 0° C. is added dropwise 37.0 grams (0.15 mole) myristoyl chloride. A precipitate of pyridinium chloride forms as the viscous mixture is stirred one hour. Upon cooling, the solid is removed by filtration and the solution is diluted with 100 mL ethyl acetate. This solution is washed four times with 50 mL 5% HCl each time, two times with 50 mL water, and dried over sodium sulfate. Filtration and evaporation of the solvent affords a residue which is refiltered through silica to yield the title composition as a solid.

Example 7

This example outlines the procedure for estimating the in vitro digestibility of the cyclohexyl diol diesters of this invention using pancreatic lipase.

Preparation of Reagents and Materials

1. Buffer: A pH 7.1 phosphate buffer is prepared by dissolving 6.8 g. $KH_2PO_4$ in 1 L. of millipore filtered water (to yield 0.05 M phosphate). Fifty mg. Ca(-NO$_3$)$_2$ and 5.0 g. cholic acid (Na salt, an ox bile isolate from Sigma) are added to give 300 microM Ca++ and 0.5 % cholic acid in 0.05 M phosphate. The pH is adjusted to approximately 7.1 with solid NaOH. Several drops of Baker "Resi-analyzed" toluene are added to prevent bacterial growth during storage at 3°–5° C.

2. Lipase: About 15 mg./mL commercial porcine pancreatic lipase from U.S. Biochemical Corporation is dissolved in buffer.

3 Substrates and Standards: A 1.0 mL volumetric flask is charged with an amount of lipid substrate (test substance or standard) calculated to give a concentration of 200 nanomoles per microliter in Baker "Resi-analyzed" toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on TLC plates (prewashed with 1:1 chloroform/methanol) by diluting the substrate solution with 10:1 toluene (1 part substrate plus 9 parts toluene) in septum vials.

Procedure

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of CHCl$_3$:CH$_3$OH and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control, this amounts to 20 nanomoles of substrate spotted on the plate.) Develop with a suitable solvent system, for example, hexane: ethyl ether: acetic acid in a ratio of 60:40:1. After 15 cm elution, dry plate with a heat gun and determine amounts of starting substrate and products of hydrolysis by scanning 10 to 20 nanomoles per channel at a wavelength of 190 nm using the CAMAG TLC Scanner II densitometer equipped with a Spectra Physics 4270 integrator and comparing with controls run at the same time.

Results

Using this procedure and enzyme system, triolein is substantially hydrolyzed in ten minutes. Cis-1,2-dimethanol dioleate prepared in Example 1 is approximately 20% hydrolyzed in three hours under the same conditions. Trans-1,2-cyclohexane dioleate prepared in Example 3 is no hydrolyzed.

Example 8

Sweet Chocolate. A low calorie sweet chocolate may be prepared by combining:

| Ingredient | parts |
|---|---|
| Cocoa Powder | 1.0 |
| Sugar | 1.0 |

To this is added a portion of

| | |
|---|---|
| Example 6 Cyclohexyl Diester | 1.0 | and the ingredients are mixed thoroughly and passed through a refiner to reduce the particles to desired size. The material is conched, and the remaining cyclohexyl diester is added. The mixture is poured into molds and quench cooled. No tempering regimen is necessary.

Chocolate Chips. The chocolate prepared above may be melted and deposited into nibs in the usual process.

Example 9

Sugar Cookies. Sugar cookies may be prepared by blending:

| Ingredient | parts |
|---|---|
| Sugar | 231 |
| Example 1 Cyclohexyl Diester | 114 |
| Salt | 3.7 |
| Sodium Bicarbonate | 4.4 |
| Water | 37.4 |
| 5.9% Dextrose Solution (wt/wt) | 58.7 |
| Flour | 391 |

All of the ingredients are creamed together. The dough so formed may be extruded (the dough is very tacky) and baked by the usual process.

Example 10

Margarine. Margarine may be prepared by combining the ingredients for the following two phases:

| | parts |
|---|---|
| Oil Phase Ingredients | |
| Example 3 Cyclohexyl Diester | 59.0 |
| Soybean Hardstock (IV 65) | 40.0 |
| Emulsifier | 1.0 |
| Aqueous Phase Ingredients | |
| Water | 95.8 |
| Milk Solids | 2.0 |
| Salt | 2.0 |
| Citric Acid | 0.1 |
| Beta Carotene | 0.1 |

The phases are emulsified in an oil:aqueous phase ratio of 80:20, and passed through a cool scraped surface heat exchanger in the usual process.

Example 11

Flavor Bits. Flavor bits for incorporation into baked goods may be prepared by combining the following ingredients:

| Ingredient | parts |
|---|---|
| Sucrose | 215 |
| Water | 180 |
| Corn Syrup | 160 |
| Example 10 Margarine | 28 |
| Flavor | 12 |
| Citric Acid | 10 |
| Glycerine | 8 |
| Salt | 5 |
| Dye | 1 |

The first three ingredients are heated to 290° F. and the heat removed. Margarine is mixed in, and the mixture allowed to cool to 160°–170° F. before adding the remaining ingredients. (Almost any flavoring material may be used as flavor, for example, butterscotch or nut.) The mixture is then poured into a cold aluminum pan and frozen in dry ice. The frozen mixture is then cracked and milled into bits.

Example 12

Butterscotch Cookies. Butterscotch cookies may be prepared by blending:

| Ingredient | parts |
|---|---|
| Flour | 22.0 |
| Example 5 Cyclohexyl Diester | 20.0 |
| Salt | 0.7 |
| Sodium Bicarbonate | 0.1 |
| Monocalcium Phosphate | 0.1 |
| Vanillin | 0.1 |
| Water | 8.0 | and mixing well. To this is added

| Sugar | 30.0 |
|---|---| which is mixed until dispersed. Then

| Butterscotch Bits from Example 11 | 19.0 |
|---|---| are added and mixed until just blended prior to depositing and baking by the usual process.

Example 13

Vanilla Wafers. To prepare vanilla wafers, blend:

| Ingredient | parts |
|---|---|
| Example 2 Cyclohexyl Diester | 25 |
| Flour | 100 |
| Granulated Sugar | 72 |
| High Fructose Corn Syrup | 5.0 |
| Nonfat Dry Milk | 1.0 |
| Salt | 1.0 |
| Ammonium Bicarbonate | 0.1 |
| Dried Egg Yolk | 1.0 |
| Water | 55 |

The dough so formed may be rolled, wire cut to ¼ inch thickness, and baked by the usual process to give a vanilla wafer cookie.

Example 14

Chocolate Chip Cookies. Chocolate chip cookies may be prepared using the butterscotch cookie recipe of Example 12, but substituting

| Ingredient | parts |
|---|---|
| Example 10 Margarine | 10.0 |
| Example 4 Cyclohexyl Diester | 10.0 | for the fat mimetic ingredient,

| Granulated Sugar | 15.0 |
|---|---|
| Brown Sugar | 15.0 | for the sugar, and

| Example 8 Chocolate Chips | 19.0 |
|---|---| for the butterscotch bits.

Example 15

Filled Cream. To make a "filled cream" composition, homogenize about

| Ingredient | parts |
|---|---|
| Example 1 Cyclohexyl Diester | 30 |
| Skim Milk | 82 |
| Polysorbate 80 | 0.1 | in a conventional dairy homogenizer.

Example 16

Ice Cream. Vanilla ice cream may be prepared by mixing

| | Ingredient | parts |
|---|---|---|
| | Sugar (10X) | 15.0 |
| | Nonfat Dry Milk | 3.9 |
| | Salt | 0.4 |
| into | Water | 39.0 | for 3 minutes. Then add melted

| Example 6 Cyclohexyl Diester | 28.4 |
|---|---| and cook to 200° F. while mixing. Hold for 1 minute. Cool to 160° F., and add

| Sugared Egg Yolks | 12.5 |
|---|---|
| Vanilla Extract | 0.8 | and mix 1 minute. Cool and freeze to desired overrun.

Example 17

Filled Milk. To prepare a "filled milk" composition, combine about

| Ingredient | parts |
| --- | --- |
| Example 15 Filled Cream | 100 |
| Skim Milk | 900 | and rehomogenzie.

Example 18

Cheese Products. To prepare cheese products, treat

Ingredient

Example 17 Filled Milk made with a 1:1 mixture of Examples 1 and 6 cyclohexyl diesters is used like natural milk in the normal cheese making process (as is practiced, for example in the production of Cheddar or Swiss cheese). Preferably add

| | parts |
| --- | --- |
| Butter Oil | 10 | to the fat mimetic portion of the filled milk product before it is employed in this process to enhance the proper flavor development of the cheese products.

Example 19

Butter Cream Icing. Butter cream icing may be prepared by blending:

| Ingredient | parts |
| --- | --- |
| Sugar | 227.0 |
| Example 4 Cyclohexyl Diester | 70.8 |
| Water | 28.4 |
| Nonfat Dry Milk | 14.0 |
| Emulsifier | 1.4 |
| Salt | 1.0 |
| Vanilla | 1.0 |

All of the ingredients are creamed in a mixer at medium speed.

Example 20

Crackers. A dough prepared by mixing together

| Ingredient | parts |
| --- | --- |
| Flour | 100 |
| Sugar | 5.0 |
| Malt | 1.5 |
| Example 2 Cyclohexyl Diester | 7.5 |
| Salt | 1.0 |
| Sodium Bicarbonate | 0.9 |
| Nonfat Dry Milk | 2.5 |
| High Fructose Corn Syrup | 2.5 |
| Monocalcium Phosphate | 0.75 |
| Water | 28 | is sheeted, stamped, and baked to produce a cracker product.

Example 21

Sprayed Crackers. The sheeted and stamped cracker dough of Example 20 may be sprayed with the cyclohexyl diester of Example 1 after baking.

Example 22

Mayonnaise. Mayonnaise can be prepared from the following formulation:

| Ingredient | parts |
| --- | --- |
| Example 5 Cyclohexyl Diester | 80 |
| Egg Yolk | 5.5 |
| Vinegar | 3.0 |
| Salt | 1.5 |
| Sugar | 2.0 |
| Flavor | 0.5 |
| Water | 7.5 |

The egg yolk is first mixed with the other dry ingredients and a small amount of the water and vinegar in a container. The cyclohexyl diester is then slowly poured into the container, while subjecting the container contents to mixing, to form an emulsion. While continuing to agitate the emulsion, the remaining water and vinegar is added.

Example 23

Pudding. Pudding can be prepared from the following formulation:

| Ingredient | parts |
| --- | --- |
| Milk | 67 |
| Sugar | 11 |
| Starch | 5 |
| Water | 9 |
| Flavor | 3 |
| Example 1 Cyclohexyl Diester | 5 |

The ingredients can be blended together to form a pudding.

Example 24

Frying Oil. The cyclohexyl diester of Example 4 with 1 ppm polydimethylsiloxane may be used for frying food snacks. For frying potatoes, omit the polydimethylsiloxane.

Example 25

Pet Food. Dry, expanded animal food kibs may be prepared from the following ingredients:

| Ingredient | parts |
| --- | --- |
| Hominy Feed | 37 |
| 52% Meat Meal | 17 |
| Wheat Shorts | 13 |
| Example 4 Cyclohexyl Diester | 16 |
| Corn Germ Meal | 9.6 |
| Wheat Germ Meal | 3 |
| Dried Milk | 0.9 |
| Beet Pulp | 1.7 |
| Fish Scrap | 0.5 |
| Brewer's Yeast | 0.5 |
| Salt | 0.5 |
| Vitamins and Minerals | 0.1 |

The ingredients are mixed together and water added to raise the water content to 27%, before extrusion, pelleting, and drying in the usual manner.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition comprising at least one food ingredient and an edible fat mimetic compound of the formula

X—Q—X, where
Q is a cyclohexane, cyclohexene or cyclohexdiene ring,
X is a —O—(CO)—R, —CH$_2$—O—(CO)—R, or —(CH$_2$)$_2$—O—(CO)—R, and each R is, independently, an aliphatic group having 1 to 29 carbons.

2. The composition according to claim 1 wherein Q is cyclohexane and X is selected from the group consisting of —O—(CO)—R and —CH$_2$—O—(CO)—R.

3. The composition according to claim 1 wherein Q is cyclohexene and X is selected from the group consisting of —O—(CO)—R and —CH$_2$—O—(CO)—R.

4. The composition according to claim 1 wherein R contains 3 to 22 carbon atoms.

5. The composition according to claim 1 wherein the R groups are derived from fatty acids selected from the group consisting of acetic, propionic, butyric, capric, caprylic, pelargonic, undecanoic, lauric, myristic, palmitic, stearic, arachidic, behenic, oleic, linoleic, linolenic, eleostearic, and arachidonic acids, and mixtures thereof.

6. The composition according to claim 1 wherein the R groups are derived from an oil selected from the group consisting of non-hydrogenated or hydrogenated sunflower, safflower, soybean, olive, sesame, peanut, palm kernel, cottonseed, palm, babassu nut, canola oil, rice bran oil, corn, and butter oils, and fractions thereof.

7. An edible, fat-containing composition having, in addition to other food ingredients, a synthetic fat mimetic compound comprising the fatty acid diesters of cyclohexanediol and cyclohexanedimethanol in full or partial replacement of natural fat.

8. The composition of claim 7 wherein said fatty acid diesters comprise C$_4$ to C$_{23}$ fatty acid diesters.

9. An edible, fat-containing composition having, in addition to other food ingredients, a synthetic fat mimetic compound comprising the fatty acid diesters of cyclohexenediol and cyclohexenedimethanol in full or partial replacement of natural fat.

10. The composition of claim 9 wherein the fatty acids comprise C$_4$ to C$_{23}$ fatty acids.

11. A method of preparing a reduced calorie fat containing food composition which comprises partially or fully replacing said fat with an edible fat mimetic compound selected from the group consisting of

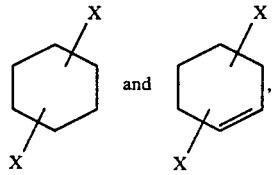

where
X is —O—(CO)—R or —CH$_2$—O—(CO)—R, and R is, independently, an aliphatic group having 1 to 29 carbons.

12. The method of claim 11 wherein said R groups have 3 to 22 carbons.

13. The method of claim 11 wherein said R groups are derived from fatty acids selected from the group consisting of butyric, caproic, caprylic, pelargonic, capric, undecanoic, lauric, myristic, palmitic, stearic, arachidic, behenic, oleic, linoleic, linolenic, eleostearic, and arachidonic acids, and mixtures thereof.

14. The method according to claim 11 wherein said R groups are derived from oils selected from the group consisting of nonhydrogenated or hydrogenated sunflower, safflower, soybean, olive, sesame, peanut, palm kernel, cottonseed, palm, babassu nut, canola oil, rice bran oil, corn, and butter oils, and fractions thereof.

15. The method of claim 11 wherein said compound is partially digestible.

16. The method of claim 11 wherein said compound provides 0.5 to 8.5 kcal per gram.

17. The method of claim 16 wherein said compound provides 1.0 to 6.0 kcal per gram.

18. A method of preparing a food composition containing an edible fat ingredient comprising incorporating a compound of the formula:

X—Q—X, where
Q is a cyclohexane or cyclohexene ring
X is —O—(CO)—R or —CH$_2$—O—(CO)—R, and
R is, independently, an aliphatic group having 1 to 29 carbons in full or partial replacement of said edible fat ingredient.

19. The composition of claim 18 wherein said R groups have 3 to 22 carbon atoms.

20. The method of claim 18 wherein said food composition is a cookie.

21. The method of claim 20 wherein said cookie further comprise sugar, salt, sodium bicarbonate, water, and flour.

22. The method of claim 20 wherein said cookie further comprises margarine and chocolate chips or butterscotch bits.

23. The method of claim 18 wherein said food composition comprises fatty candy.

24. The method of claim 23 wherein said candy comprises chocolate.

25. The method of claim 24 wherein said chocolate further comprises cocoa powder and sugar.

26. The method of claim 25 wherein said chocolate is further processed to form chocolate chips.

27. The method of claim 18 wherein said food composition comprises a dairy product.

28. The method of claim 27 wherein said dairy product is selected from the group consisting of filled cream and filled milk.

29. The method of claim 28 wherein said dairy product further comprises skim milk.

30. The method of claim 27 wherein said dairy product is ice cream.

31. The method of claim 30 wherein said ice cream further comprises skim milk, sugar, gelatin, flavor and color.

32. The method of claim 27 wherein said dairy product is a cheese product.

33. The method of claim 18 wherein said food composition is butter cream icing.

34. The method of claim 33 wherein said butter cream icing further comprises sugar, water, non-fat dry milk, emulsifier, salt and vanilla.

35. The method of claim 18 wherein said food composition is a cracker.

36. The method of claim 35 wherein said cracker further comprises flour, sugar, malt, sodium bicarbonate, non-fat dry milk, high fructose corn syrup, monocalcium phosphate and water.

37. The method of claim 18 wherein said food composition is mayonnaise.

38. The method of claim 37 wherein said mayonnaise further comprises egg yolk, vinegar, salt, sugar, flavor, and water.

39. The method of claim 18 wherein said food composition is a pudding.

40. The method of claim 39 wherein said pudding further comprises milk, sugar, starch, water and flavor.

41. The method of claim 18 wherein said food composition is a frying oil.

42. The method of claim 18 wherein said food composition comprises a pet food.

43. The method of claim 42 wherein said pet food further comprises hominy feed, meat meal, wheat shorts, corn germ meal, wheat germ meal, dried milk, beet pulp, brewer's yeast, salt, vitamins and minerals.

44. The method of claim 18 wherein said food composition comprises margarine.

45. The method of claim 44 wherein said margarine further comprises soybean hardstock, emulsifier, water, milk solids, salt, citric acid, and beta carotene.

46. In a food composition containing a digestible fat ingredient, an improvement wherein at least a portion of the digestible fat ingredient is replaced by a compound having a six-carbon cyclic backbone to which are attached two fatty acid residues in ester linkage with or without an intervening methylene group.

47. The improvement of claim 46 wherein said backbone has no double bonds and said residues are $C_4$ to $C_{23}$ fatty acid residues.

48. The improvement of claim 46 wherein said backbone has one double bond and said residues are $C_4$ to $C_{23}$ fatty acid residues.

49. The improvement of claim 46 wherein said 80% or more of said residues are derived from fatty acids having 18 carbon atoms.

50. An edible, fat-containing composition comprising, in addition to other food ingredients, cyclohexane dioleate in full or partial replacement of natural fat.

51. An edible, fat-containing composition comprising, in addition to other food ingredients, cyclohexanedimethane dioleate in full or partial replacement of natural fat.

52. An edible, fat-containing composition comprising, in addition to other food ingredients, cyclohexene dioleate in full or partial replacement of natural fat.

53. An edible, fat-containing composition comprising, in addition to other food ingredients, cyclohexenedimethane di-10-undecenate in full or partial replacement of natural fat.

54. An edible, fat-containing composition comprising, in addition to other food ingredients, cyclohexanedimyristate in full or partial replacement of natural fat.

* * * * *